(12) United States Patent
White et al.

(10) Patent No.: US 6,994,710 B2
(45) Date of Patent: Feb. 7, 2006

(54) SURGICAL DRIVER

(76) Inventors: Patrick Michel White, 1213 Indian Trail Dr., Downingtown, PA (US) 19335; André Lechot, Sous l'Eau Belle 24, 2534 Orvin (CH)

(*) Notice: Subject to any disclaimer, the term of this patent is extended or adjusted under 35 U.S.C. 154(b) by 0 days.

(21) Appl. No.: 10/141,504

(22) Filed: May 8, 2002

(65) Prior Publication Data

US 2002/0198534 A1    Dec. 26, 2002

Related U.S. Application Data

(60) Provisional application No. 60/289,685, filed on May 9, 2001.

(51) Int. Cl.
*A61B 17/88* (2006.01)
(52) U.S. Cl. .................................................. 606/104
(58) Field of Classification Search ................ 606/104, 606/99, 96; 81/52, 436, 438, 451–453
See application file for complete search history.

(56) References Cited

U.S. PATENT DOCUMENTS

| | | | |
|---|---|---|---|
| 4,535,658 A | * | 8/1985 | Molinari ..................... 81/438 |
| 5,309,798 A | * | 5/1994 | Markwart et al. ............ 81/438 |
| 5,531,143 A | * | 7/1996 | Habermehl et al. .......... 81/438 |
| 6,009,779 A | * | 1/2000 | Mastroni ..................... 81/438 |
| 6,302,001 B1 | * | 10/2001 | Karle ........................... 81/436 |

FOREIGN PATENT DOCUMENTS

| | | | |
|---|---|---|---|
| GB | 2377641 A | * | 1/2003 |
| WO | WO 9919119 A1 | * | 4/1999 |

* cited by examiner

*Primary Examiner*—Eduardo C. Robert
*Assistant Examiner*—Jessica R. Baxter
(74) *Attorney, Agent, or Firm*—Moetteli & Associes Sarl; John Moetteli (57) ABSTRACT

A surgical instrument is disclosed having a male portion with a tapered hexagonal tip for engaging a socket head screw. A shaft operatively carries the male portion, for transmitting torque to the tip as it is matingly engaged with the screw. A metallic ring, mounted on the male portion, removably retains the tip matingly engaged within the socket head. The ring is formed with an oblique slit and is radially compressible, the ring presenting a substantially continuous circumferential surface that is in interference fit within the socket.

27 Claims, 6 Drawing Sheets

SURGICAL DRIVER

This appln claims benefit of 60/289,685, May 9, 2001.

BACKGROUND OF THE INVENTION

The present invention relates generally to instrumentation used for driving screws during surgery, more specifically, the present invention is suitable for medical applications involving orthopedic implants.

One of the present inventors has previously filed Swiss application no. 0839/99 on May 5, 1999, the disclosure of which is reproduced here in relevant part and incorporated herein by reference thereto. In this application there is disclosed an annular metallic ring that is perpendicularly slit, to exert a holding force against the internal wall of the socket head of a screw. However, the ring had a tendency for the free ends of the open slit to become skewed relative to one another during use. Moreover, the straight tip of the driver did not always exert uniform contact with the mating female socket wall to transfer torque without significant rotational play within the socket. This is disadvantageous to surgeons who require an instrument that gives them a precise feel for where they are placing the screw. Instruments of this type are typically manually driven either by a handle grasped by the surgeon, or, they can be connected to a powered hand tool. The screw must be securely held while pre-assembled with the male end of the tool during interoperative insertion. The surgeon must have precise control without risking that the screw will separate from the tool and fall out, e.g., while manipulating it before it is driven into the bone.

It is known to use a driver with tapered tip that seeks to wedge into the socket head of a driven screw; however, this approach did not use retaining rings to hold the driver and screw together during placement. As a result, if the tolerances weren't just right the weight of the screw would overcome the wedging force keeping the driver tip in the socket, so the screw tended to fall unpredictably off the tip during surgery.

Another prior design of the present inventor employs the C-shaped ring, mentioned above, to temporarily hold the cutting tip of a modular flexible reaming system onto the shaft. This allows the assembly to be passed from a nurse to the surgeon without the components falling apart onto the non-sterile floor. It also allows the nurse to change the tip from one size to another rapidly, as the surgeon progressively reams a bone canal. It is contemplated that a C-shaped ring can be useful as a pre-tensioning member in such a temporary male-female assembly. However, the present inventor has generally observed that this problem occurs whenever a C-shaped ring is used to hold a male and female member together temporarily. The ring can still catch on the entrance to the female socket, causing the connection to malfunction. Conversely, if the ring is mounted inside the female socket, i.e., instead of on the male tip, the present inventor believes that similar problems would result.

Accordingly, there is a need for a tool with a retaining ring that temporarily holds together a driving member and a driven member, e.g., a driven screw, where the ring has no exposed edges that might cock the tip in the socket and thus impair operation. Similarly, this need extends to other surgical applications, such as temporary retention of a reamer cutting tip with a shaft.

There is a further need for providing a driving tool that has improved wedging contact between the tip and socket head to give a solid feel to the surgeon's hand during an operation, while securely holding the screw and tip together during surgical placement.

SUMMARY OF INVENTION

According to an embodiment of the present invention, a surgical instrument is disclosed, having a male portion with a tip for engaging a socket head of a screw. A shaft operatively carries the male portion, for transmitting torque to the tip as it is matingly engaged with the screw. A metallic ring, mounted on the male portion, removably retains the tip matingly engaged within the socket head. The ring is formed with an oblique slit and is radially compressible, the ring presenting a substantially continuous circumferential surface that is in interference fit within the socket.

In a preferred embodiment of the present invention, the ring has a substantially rounded cross-section.

In another preferred embodiment, the ring has a toroid cross-section.

In yet another embodiment of the present invention, a surgical instrument is disclosed having a male portion with a tapered tip for engaging a socket head screw. A shaft operatively carries the male portion, for transmitting torque to the tip as it is matingly engaged with the screw. A metallic ring, mounted on the male portion, removably retains the tip matingly engaged within the socket head. The ring is formed with a slit and is radially compressible, the ring being in an interference fit within the socket.

In still another embodiment of the present invention, a surgical instrument is disclosed having a male portion with a tapered hexagonal tip for engaging a socket head screw. A shaft operatively carries the male portion, for transmitting torque to the tip as it is matingly engaged with the screw. A metallic ring, mounted on the male portion, removably retains the tip matingly engaged within the socket head. The ring is formed with an oblique slit and is radially compressible, the ring presenting a substantially continuous circumferential surface that is in interference fit within the socket.

In yet still another embodiment of the present invention, a surgical instrument is disclosed. The instrument has a male portion with a tip for engaging a socket and a metallic ring. The ring is mounted on the male portion, for removably retaining the tip matingly engaged within the socket. The ring is formed with an oblique slit and is radially compressible, the outside of the ring presenting a substantially continuous surface that is in an operative interference fit within the socket.

In yet still another embodiment of the present invention, a surgical instrument is disclosed. The instrument has a male portion with a tip for engaging a socket; and a metallic ring, mounted in the socket, for removably retaining the tip matingly engaged within the socket, wherein the ring is formed with an oblique slit and is radially compressible, the inside of the ring presenting a substantially continuous surface that is in an operative interference fit with the tip.

In another embodiment, the ring has a substantially rounded cross-section.

In another embodiment, the ring has a toroid cross-section.

In another embodiment, the ring and the slit have respective dimensions selected to pretension the inside of the ring against the tip sufficiently to retain the tip and socket matingly engaged with one another during a surgical operation.

In another embodiment, the tip and socket have correspondingly-shaped mating cross-sections.

In another embodiment, the tip has a cross-section selected from the group comprising polygonal, torx, cloverleaf or star shapes.

An advantage of an embodiment of the present invention is that the obliquely slit ring has no exposed edges that can catch within the socket and otherwise cock the ring and skew the tip.

Another advantage of another embodiment of the present invention is that a tapered tip wedges into mating contact with the socket to minimize play as the mating tip and socket are fully engaged; moreover, the ring holds the tip in engagement with the socket so the screw can be set manually wherever desired during surgery.

Other objects and advantages will be appreciated by those skilled in the art, by resort to the appended Drawings having reference numerals that correspond to the ensuing Description of one or more embodiments of the invention wherein the following Figures are further elucidated.

DETAILED DESCRIPTION OF THE DRAWINGS

Figure 1:
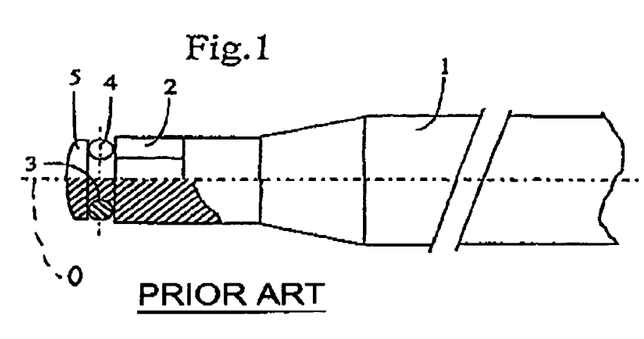
FIG. 1 is an external side view partially cut away to show a male end with tip having a C-shaped ring of the inventor's prior design.
Figure 2:
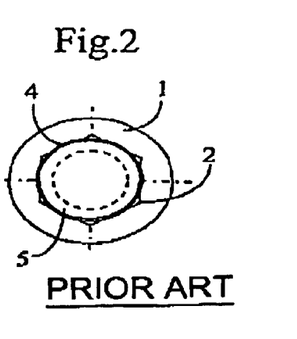
FIG. 2 is an end view of FIG. 1, showing the hexagonal tip and retaining ring (in phantom)
Figure 3:
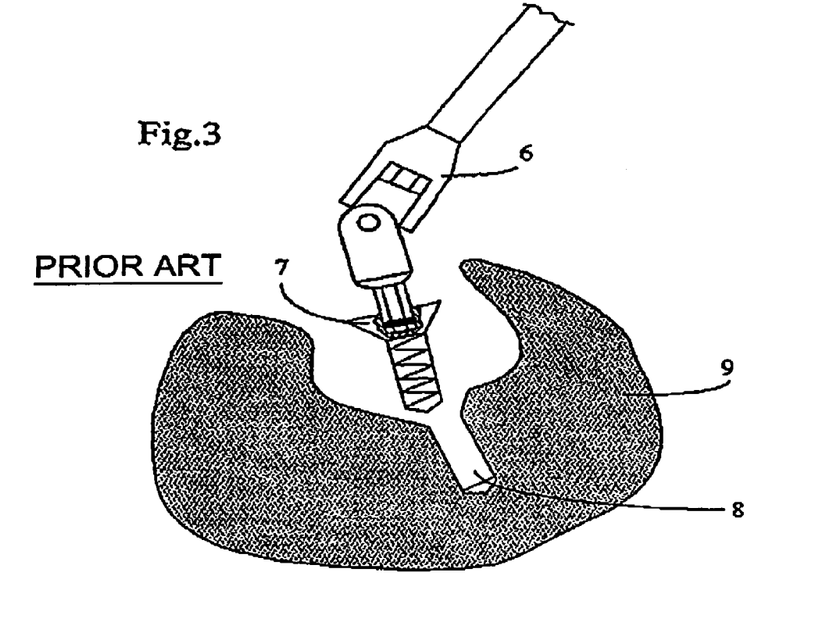
FIG. 3 is a perspective view schematically representing the inventor's prior tool in operation during an arthroplasty procedure, showing in partial cross-section the screw held by the male end of the tool.
Figure 4:
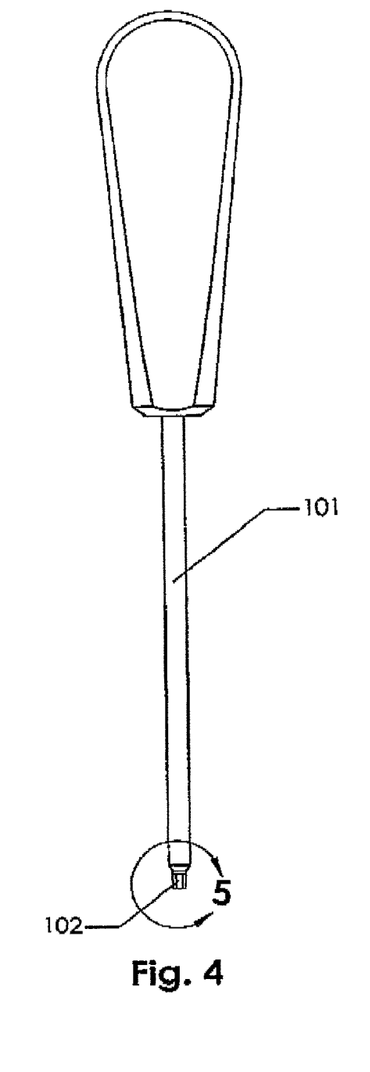
FIG. 4 is a side view of the entire tool of the inventor's prior design.
Figure 5:
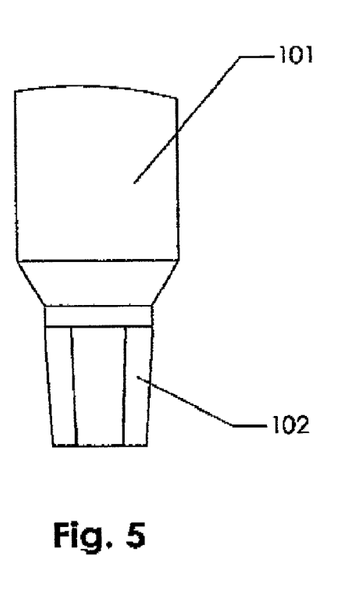
FIG. 5 is an enlarged view of the circled region 5 of the male end shown in FIG. 4, detailing the tapered hexagonal tip without a retaining ring.
Figure 6:
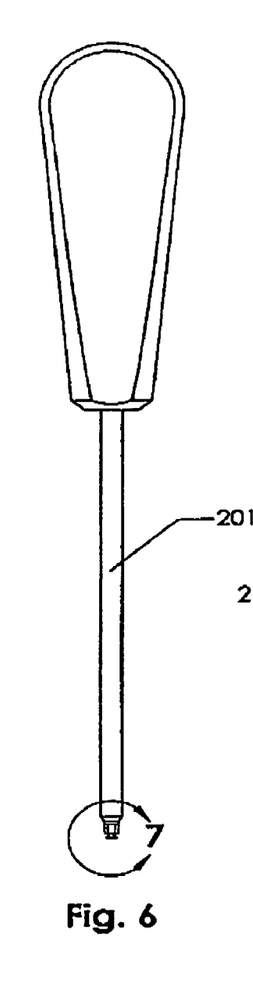
FIG. 6 is side view of the surgical instrument of the invention.
Figure 7:
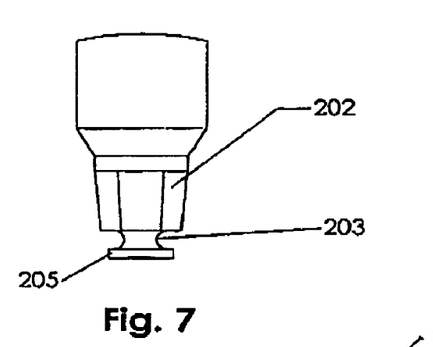
FIG. 7 is an enlarged view of the circled region 6 of the male end shown in FIG. 6, detailing the tapered hexagonal tip without the retaining ring in place.
Figures 8, 9, 9A:
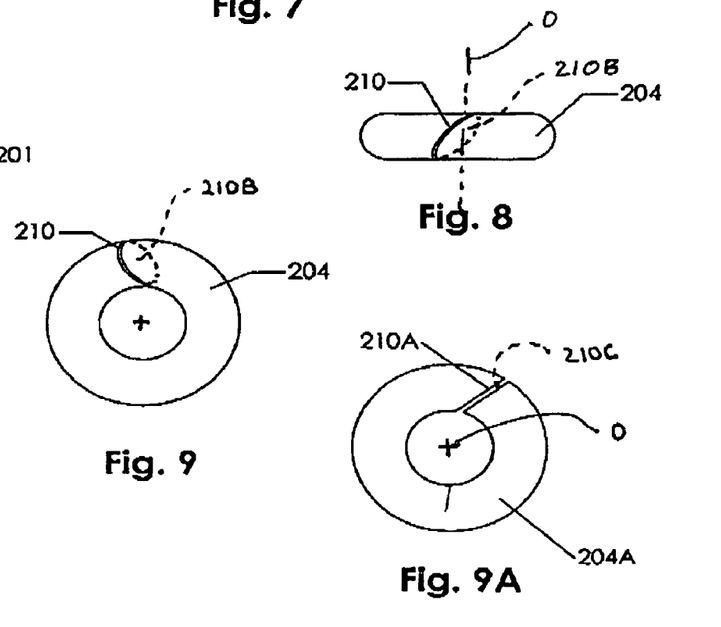
FIG. 8 is a side view of the retaining ring of the invention.
FIG. 9 is a top view of the retaining ring of a FIG. 8, showing the oblique slit in the ring.
Figure 10:
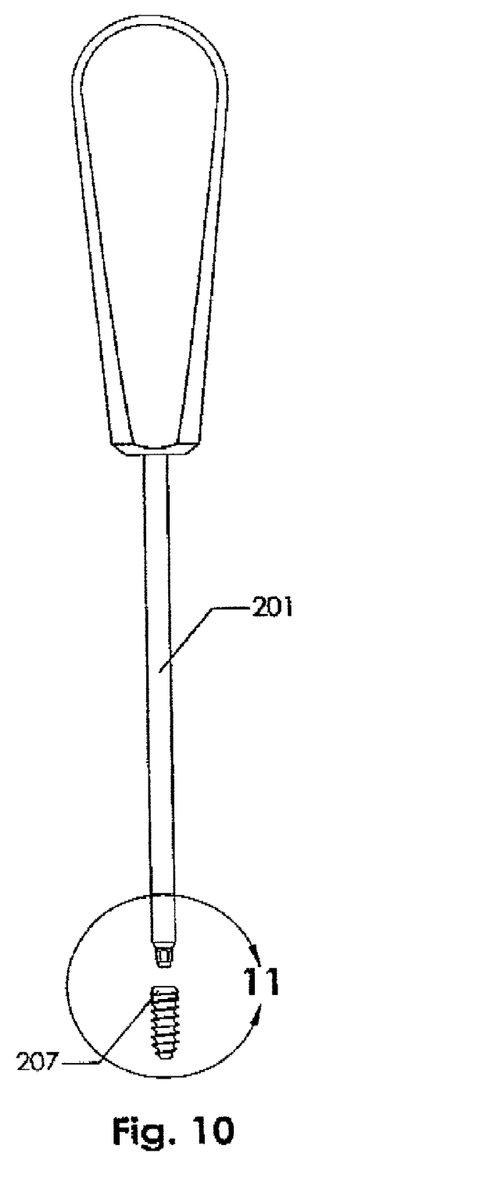
FIG. 10 is an exploded side view of an instrument of the invention prior to insertion of the tip into the socket head of a driven screw.
Figure 11:
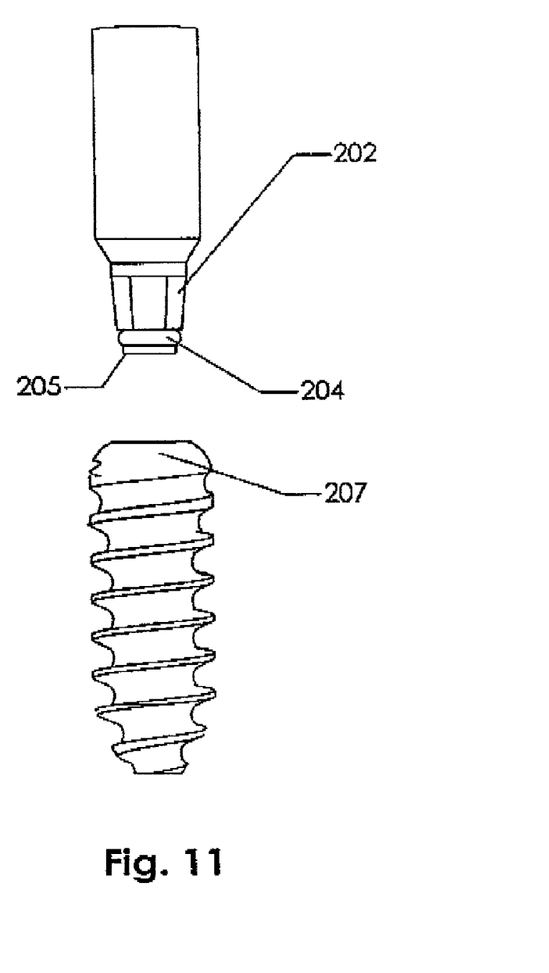
FIG. 11 is an enlarged view of the circled region 11 of FIG. 10, showing the male end with tip having a retaining ring mounted distally from the tapered hexagonal facets of the tip.
Figure 12:
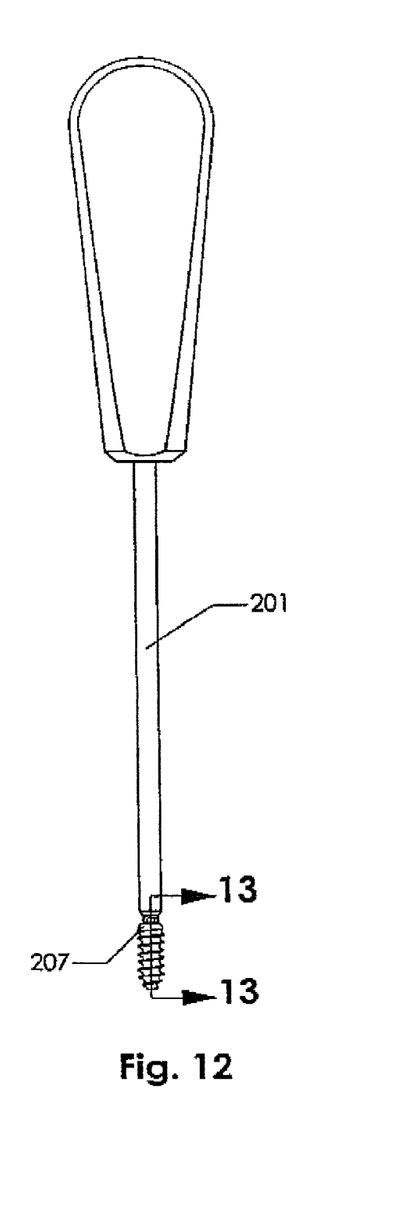
FIG. 12 is a side view of an instrument of the invention with a tapered tip pre-assembled to the socket head of the driven screw.

Referring to FIGS. 1–3, the inventor's prior design included a shaft 1 with hexagonal tip 2 and ring 4 shown with a C-shape and having ends forming an open slit there-between mounted within a groove 3 in the tip 2. A distal groove defined by a terminal protrusion 5 provided to mount the ring. Once pre-assembled, the screw 7 is manipulated into position by the surgeon using the tool, for example, by a handle at the end of swivel-mounted shaft 6. The object of the surgeon is to manipulate the screw 7 within, e.g., the cavity of bone 9, in order to insert the screw into an orifice 8 which can be the bore of an implanted prosthetic component or formed in the bone itself. FIGS. 4–5 show a prior design with tapered tip 102 on male end 101, without retaining ring mounted thereon. Although the tapered tip 102 does provide a measure of wedging action against a socket head (not shown), if the tolerances aren't just right the screw can still fall off the tip 2 during surgical manipulation.

Referring to FIGS. 6–9, 9A, a surgical instrument of the invention is disclosed, having a male portion with a tip 202 for engaging a socket head of a screw (FIGS. 10–13). A shaft 201 operatively carries the male portion (circled region 7), for transmitting torque to the tip 202 as it is matingly engaged with the screw. A metallic ring 204, 204A, mounted on the male portion within groove 203 between tip 202 and protrusion 205, removably retains the tip matingly engaged within the socket head. The ring is formed with an oblique slit 210, 210A and is radially compressible to exert a predetermined tension. The ring 204 presents a substantially continuous circumferential surface that is in interference fit within the socket 212. The ring 204, 204A and the slit 210, 210A have respective dimensions selected to pretension the ring against an internal wall of the socket head 212 (FIG. 13) sufficiently to retain the tip 202 and screw 207 matingly engaged with one another during a surgical operation. Because the slit 210 is oblique, rather than perpendicular as in the Applicant's prior design, there are no exposed ends that tend to catch on the socket and cause the ring to become skewed. As a result, the tip 202 is held securely and in proper axial alignment within the socket so that the weight of the screw 207 does not cause it to fall off (FIGS. 10–13).

Each type of oblique slit 210, 210A defines substantially flat, facing end surfaces 210B and 210C, respectively. Such surfaces are oriented within substantially parallel planes which, when compressed together, do not contain the central axis 0 of the ring 204. In other words, the oblique slit 210, 210A lies in a plane inclined from a plane which includes a point on the slit and the central axis 0 of the ring. In the embodiment shown in FIGS. 8 and 9, the end surfaces 210B are oriented substantially non-parallel to the axis 0 as well. In the embodiment shown in FIG. 9A, the surfaces 210C, although parallel with the central axis 0, are not coplanar therewith.

In a preferred embodiment of the present invention, the ring 204 has a substantially rounded cross-section, still preferably a toroid cross-section (FIGS. 6–13). The cross-section of ring 204 could be uniformly toroid or generally rounded distally of the tip and flattened proximally. The ring 204 could also have a polygonal cross-section, but since the ring does not function to transmit torque, the toroid shape adequately holds the tip frictionally in place against the preferred hexagonal socket head.

The tip 202 preferably has a hexagonal, but could also have other polygonal or clover shapes (not shown).

Figure 13:
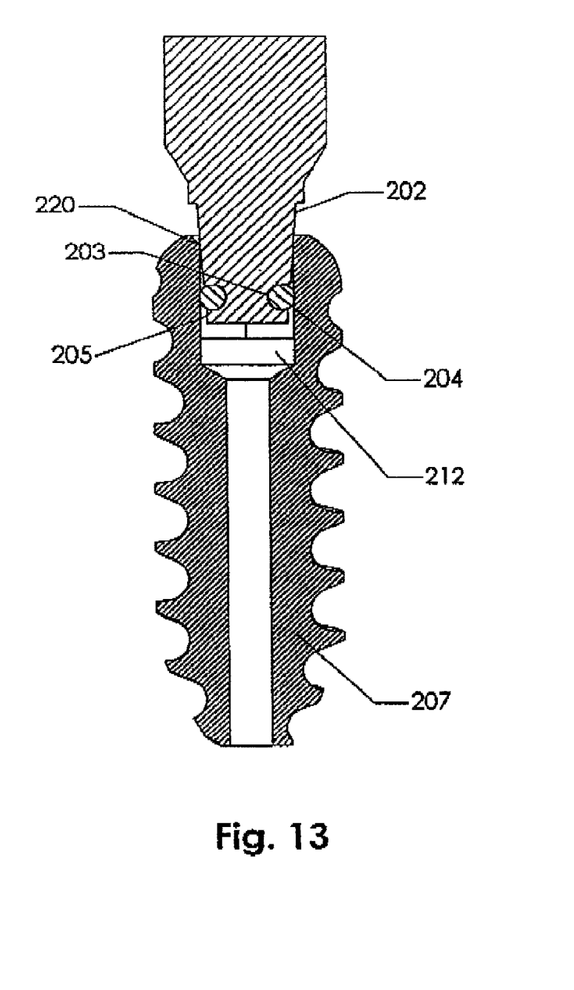
FIG. 13 is a partial cross-sectional view, taken at Lines 13—13 of FIG. 12, showing the tapered tip wedged into the socket head and retaining ring in an interference fit with the female wall of the socket head.
Figure 14A:
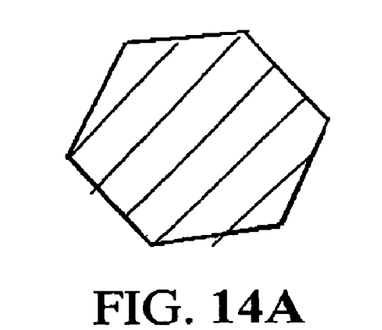
FIG. 14A is a cross section of a hexagonal drive used in the invention.
Figure 14B:
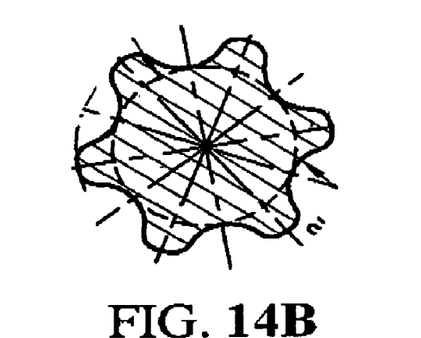
FIG. 14B is a cross section of a torx or star drive.
Figure 14C:
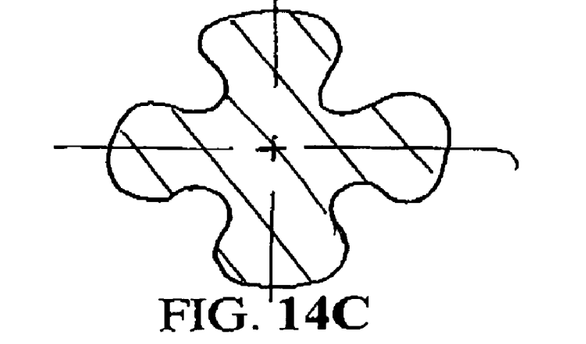
FIG. 14C is a cross section of a clover-leaf drive.
Figure 14D:
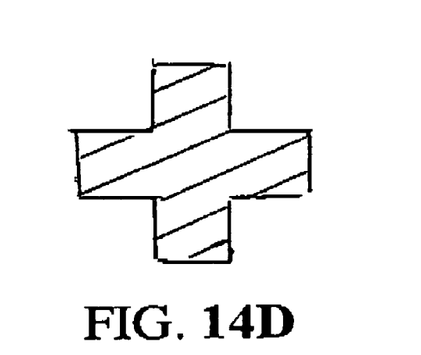
FIG. 14D is a cross-section of a cross-shaped drive.

Referring to FIGS. 10–13, a surgical instrument is disclosed having a male portion with a tapered tip 202 for engaging socket head screw 207, particularly in the region of wedging contact indicated at 220 in FIG. 13. A shaft 201 operatively carries the male portion, for transmitting torque to the tip 202 as the tip is matingly engaged with the screw 207. A metallic ring 204 is mounted on the male portion in groove 203 formed between tip 202 and terminal protrusion 205. The ring 204 removably retains the tip 202 matingly engaged within the socket 212. The ring 204 is formed with a slit 210 and is radially compressible, the ring being in a pre-determined interference fit within the socket 212. The slit 210 may be C-shaped, as in the inventor's earlier design, but preferably it is an oblique slit as shown in FIGS. 6–9. The ring is mounted in the groove formed by protrusion 205.

Although illustrative embodiments of the invention have been shown and described, a wide range of modification, change and substitution is contemplated in the foregoing disclosure and in some instances, some features of the present invention may be employed without a corresponding use of the other features. Accordingly, it is appropriate that the appended claims be construed broadly and in a manner consistent with the scope of the invention.

The invention claimed is:

1. A surgical instrument comprising:
   a male portion with a tip for engaging a female socket of a socket head of a screw;
   a shaft operatively carrying the male portion, for transmitting torque to the tip as the tip is matingly engaged with the screw; and
   a metallic ring, mounted on the male portion, for removably retaining the tip when the tip is matingly engaged within the socket head, wherein the ring is formed with an oblique slit defined between substantially parallel, opposed, adjacent surfaces of the ring, each surface lying in a plane substantially inclined from a plane which includes a point on the respective surface and the central axis of the ring, thus enabling the ring to be radially compressible, and presenting a substantially continuous circumferential surface that is in interference fit within the socket when the socket is attached.

2. The instrument of claim 1 wherein the ring has a substantially rounded cross-section.

3. The instrument of claim 1 wherein the ring has a toroid cross-section.

4. The instrument of claim 1 wherein the ring and the slit have respective dimensions selected to pretension the ring against an internal wall of the socket head sufficiently to retain the tip and screw matingly engaged with one another during a surgical operation.

5. The instrument of claim 4 wherein the tip and socket head have correspondingly-shaped mating cross-sections.

6. The instrument of claim 5 wherein the tip is tapered for wedging contact with a corresponding female tapered surface of the socket head.

7. The instrument of claim 5 wherein the tip has a cross-section selected from a group of cross-sections consisting of polygonal, torx, cloverleaf and star cross-sections.

8. A surgical instrument comprising:
   a male portion with a tapered tip for engaging a socket;
   a shaft operatively carrying the male portion, for transmitting torque to the tip when it is matingly engaged within the socket; and
   a metallic ring, mounted an the male portion, for removably retaining the tip when matingly engaged within the socket, wherein the ring is formed with an oblique slit defined between substantially parallel, opposed, adjacent surfaces of the ring, each surface lying in a plane substantially inclined from a plane which includes a point on the respective surface and the central axis of the ring, thus enabling the ring to be radially compressible, the ring capable of forming an interference fit within the socket when the socket is attached.

9. The instrument of claim 8 wherein the ring has an oblique slit with a dimension selected to pretension the ring against an internal wall of the socket head when engaged therewith, sufficiently to retain the tip and screw matingly engaged with one another during a surgical operation.

10. The instrument of claim 8 wherein the ring has a substantially rounded cross-section.

11. The instrument of claim 8 wherein the ring has a toroid cross-section.

12. The instrument of claim 8 wherein the tip has a cross-section selected from a group of cross-sections consisting of polygonal, torx, cloverleaf and star shaped cross-sections.

13. A surgical instrument comprising:
    a male portion with a tapered hexagonal tip for engaging a socket head of a socket head screw;
    a shaft operatively carrying the male portion, for transmitting torque to the tip when the tip is matingly engaged with the socket head; and
    a metallic ring, mounted on the male portion, for removably retaining the tip when matingly engaged within the socket head, wherein the ring is formed with an oblique slit defined between substantially parallel, opposed, adjacent surfaces of the ring, each surface lying in a plane substantially inclined from a plane which includes a point on the respective surface and the central axis of the ring, thus enabling the ring to be radially compressible, the ring presenting a substantially continuous circumferential surface capable of forming an interference fit within the socket head when the socket is attached.

14. The instrument of claim 13 wherein the ring has a substantially rounded cross-section.

15. The instrument of claim 13 wherein the ring has a toroid cross-section.

16. A surgical instrument comprising:
    a male portion with a tip for engaging a socket; and
    a metallic ring having an outer surface, mounted on the male portion, for removably retaining the tip when matingly engaged within the socket, wherein the ring is formed with an oblique slit defined between substantially parallel, opposed, adjacent surfaces of the ring, each surface lying in a plane substantially inclined from a plane which includes a point on the respective surface and the central axis of the ring, thus enabling the ring to be radially compressible, the outer surface of the ring presenting a substantially continuous surface that is capable of forming an operative interference fit within the socket when the socket is attached.

17. The instrument of claim 16 wherein the ring has a substantially rounded cross-section.

18. The instrument of claim 16 wherein the ring has a toroid cross-section.

19. The instrument of claim 16 wherein the ring and the slit have respective dimensions so that, when engaged with a corresponding socket head, the outside of the ring is pretensioned against an internal wall of the socket head sufficiently to retain the tip and socket head matingly engaged with one another during a surgical operation.

20. The instrument of claim 19 wherein the tip and socket have correspondingly-shaped mating cross-sections.

21. The instrument of claim 20 wherein the tip has a cross-section selected from a group of cross-sections consisting of polygonal, torx, cloverleaf and star shapes.

22. A surgical instrument comprising:

a male portion with a tip for engaging a socket;

a metallic ring having an inside surface, mounted in the socket, for removably retaining the tip matingly engaged within the socket, wherein the ring is formed with an oblique slit defined between substantially parallel, opposed, adjacent surfaces of the ring, each surface lying in a plane substantially inclined from a plane which includes a point on the respective surface and the central axis of the ring, thus enabling the ring to be radially compressible, the inside surface of the ring presenting a substantially continuous surface that is capable of forming an operative interference fit with the tip when a socket is attached.

23. The instrument of claim 22 wherein the ring has a substantially rounded cross-section.

24. The instrument of claim 22 wherein the ring has a toroid cross-section.

25. The instrument of claim 22 wherein the ring and the slit have respective dimensions selected to pretension the inside of the ring against the tip sufficiently to retain the tip and socket matingly engaged with one another during a surgical operation.

26. The instrument of claim 25 wherein the tip and socket have correspondingly-shaped mating cross-sections.

27. The instrument of claim 26 wherein the tip has a cross-section selected from a group of cross-sections consisting of polygonal, torx, cloverleaf and star shape.

* * * * *